United States Patent
Dalley et al.

(10) Patent No.: US 11,642,272 B2
(45) Date of Patent: May 9, 2023

(54) MOBILITY ASSISTANCE DEVICES WITH AUTOMATED ASSESSMENT AND ADJUSTMENT CONTROL

(71) Applicant: Ekso Bionics Holdings, Inc., San Rafael, CA (US)

(72) Inventors: Skyler Dalley, Macedonia, OH (US); Spencer Murray, Macedonia, OH (US); Ryan Farris, Solon, OH (US); Michael Goldfarb, Nashville, TN (US); Scott Morrison, Macedonia, OH (US)

(73) Assignee: Ekso Bionics Holdings, Inc., San Rafael, CA (US)

( * ) Notice: Subject to any disclaimer, the term of this patent is extended or adjusted under 35 U.S.C. 154(b) by 1045 days.

(21) Appl. No.: 16/344,643

(22) PCT Filed: Feb. 7, 2018

(86) PCT No.: PCT/US2018/017174
§ 371 (c)(1),
(2) Date: Apr. 24, 2019

(87) PCT Pub. No.: WO2018/175004
PCT Pub. Date: Sep. 27, 2018

(65) Prior Publication Data
US 2020/0060921 A1 Feb. 27, 2020

Related U.S. Application Data

(60) Provisional application No. 62/474,764, filed on Mar. 22, 2017.

(51) Int. Cl.
*A61H 3/00* (2006.01)
*A61F 5/01* (2006.01)
(Continued)

(52) U.S. Cl.
CPC ........... *A61H 3/008* (2013.01); *A61F 5/0123* (2013.01); *A61H 1/0262* (2013.01);
(Continued)

(58) Field of Classification Search
CPC .......... A61H 3/00–068; A61H 2003/001–065; A61H 1/0262; A61H 2201/165;
(Continued)

(56) References Cited

U.S. PATENT DOCUMENTS

| 6,280,380 B1 | 8/2001 | Bardy | |
| 2008/0234608 A1* | 9/2008 | Sankai | B25J 9/0006 601/5 |
| 2009/0210093 A1* | 8/2009 | Jacobsen | A61H 3/00 700/260 |

FOREIGN PATENT DOCUMENTS

| CN | 101623547 A | 1/2010 |
| CN | 104013513 A | 9/2014 |

(Continued)

OTHER PUBLICATIONS

International Search Report and Written Opinion of PCT/US2018/017174 dated May 15, 2018.

(Continued)

*Primary Examiner* — Valerie L Woodward
*Assistant Examiner* — Paige Kathleen Bugg
(74) *Attorney, Agent, or Firm* — Renner, Otto, Boisselle & Sklar, LLP

(57) ABSTRACT

A method of controlling a mobility device and related device including at least one actuator component that drives at least one joint component is described. The control method may include executing a control application with an electronic controller to perform: receiving a command in the control system of the mobility device for initiating an automated assessment and adjustment protocol; controlling one or more
(Continued)

mobility device components to perform the automated assessment; electronically gathering user performance data associated with the automated assessment and determining user performance metrics; and electronically controlling one or more of the mobility device components in accordance with the performance metrics. The automated assessment includes controlling mobility device components to perform a predetermined assessment activity related to performance of the mobility device and/or user. Automatic adjustments to the device components, including adjusting tension and resistance levels of the joint components, may then be made based the performance metrics.

16 Claims, 12 Drawing Sheets

(51) Int. Cl.
  *B25J 9/00* (2006.01)
  *A61H 1/02* (2006.01)
(52) U.S. Cl.
  CPC ....... *B25J 9/0006* (2013.01); *A61H 2003/007* (2013.01); *A61H 2201/1207* (2013.01); *A61H 2201/165* (2013.01); *A61H 2201/1642* (2013.01); *A61H 2201/5084* (2013.01)
(58) Field of Classification Search
  CPC ........ A61H 2201/5058–5084; A61H 2205/10–108; B25J 9/0006
  USPC ............................................................ 601/5
  See application file for complete search history.

(56) References Cited

FOREIGN PATENT DOCUMENTS

| | | | |
|---|---|---|---|
| CN | 104698848 A | 6/2015 | |
| CN | 105288933 A | 2/2016 | |
| DE | 4027317 C1 | 12/1991 | |
| KR | 20140040309 A | 4/2014 | |
| WO | WO-2013142777 A1 * | 9/2013 | ............. A61B 5/112 |
| WO | WO-2014159577 A1 * | 10/2014 | ........... A61B 5/1124 |
| WO | WO 2015/164421 A1 | 10/2015 | |
| WO | WO 2017/035512 A1 | 3/2017 | |

OTHER PUBLICATIONS

Bing Chen et al.: "Recent developments and challenges of lower extremity exoskeletons", Journal of Orthopaedic Translation, vol. 5, pp. 26-37, 2016, http://dx.doi.org/10.1016/j.jot.2015.09.007.

Shahid Hussain et al.: "Adaptive Impedance Control of a Robotic Orthosis for Gait Rehabilitation", IEEE Transactions on Cybernetics, vol. 43, No. 3, Jun. 2013.

Hugo A. Quintero, MS et al.: "A Powered Lower Limb Orthosis for Providing Legged Mobility in Paraplegic Individuals", Top Spinal Cord Inj Rehabil. 2011; 17(1): 25-33. doi:10.1310/sci1701-25.

Clare Hartigan, MPT et al.: "Mobility Outcomes Following Five Training Sessions with a Powered Exoskeleton", Top Spinal Cord Inj Rehabil 2015;21(2):93-99, doi: 10.1310/sci2102-93.

Antonio J. del-Ama et al.: "Hybrid gat training with an overground robot for people with incomplete spinal cord injury: a pilot study", Frontiers in Human Neuroscience, vol. 8, Article 298, May 2014, doi: 10.3389/fnhum.2014.00298.

* cited by examiner

MOBILITY ASSISTANCE DEVICES WITH AUTOMATED ASSESSMENT AND ADJUSTMENT CONTROL

RELATED APPLICATION DATA

This application is a national stage application pursuant to 35 U.S.C. § 371 of PCT/US2018/017174 filed on Feb. 7, 2018, which claims the benefit of U.S. Provisional Application No. 62/474,764 filed Mar. 22, 2017, the contents of which are which is incorporated herein by reference.

FIELD OF INVENTION

The present invention relates to electronic control systems for a mobility assistance device, such as for example a legged mobility device or "exoskeleton" device, including control systems for assessing and adjusting the operation of the legged mobility device or exoskeleton device or other mobility assistance device.

BACKGROUND OF THE INVENTION

There are currently on the order of several hundred thousand spinal cord injured (SCI) individuals in the United States, with roughly 12,000 new injuries sustained each year at an average age of injury of 40.2 years. Of these, approximately 44% (approximately 5300 cases per year) result in paraplegia. One of the most significant impairments resulting from paraplegia is the loss of mobility, particularly given the relatively young age at which such injuries occur. Surveys of users with paraplegia indicate that mobility concerns are among the most prevalent, and that chief among mobility desires is the ability to walk and stand. In addition to impaired mobility, the inability to stand and walk entails severe physiological effects, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities. In addition to full paraplegia, debilitative health conditions, like strokes and other vascular and neurological impairment, can substantially impair mobility and have the additional secondary physiological effects.

In view of the need to address mobility impairment, various assessments of physical capability have been developed. Once common assessment is the "Manual Muscle Test" (MMT), which is a common functional strength assessment in which a test subject attempts specific motions in a variety of positions, with varying levels of resistance, to grade muscle strength. The MMT requires equipment to facilitate positioning the subject (e.g. mats, chairs, or blocks), and requires a test administrator to position and instruct the subject, observe muscle tone and joint motion, provide movement resistance, and determine muscle grading. To perform the MMT in a conventional manner, the test subject attempts movement of a specific muscle perpendicular to gravity (i.e. in the horizontal plane). An example is contracting the hamstring to observe motion about the knee, which requires the subject to lie on their side. The test administrator then palpates the test subject's muscle while observing whether or not motion actually occurs. If the muscle contracts, and its corresponding joint moves through its full range of motion, the same movement is then attempted parallel to gravity (i.e. in the vertical plane). If the test subject can maintain muscle contraction against gravity, the same movement is attempted against increasing levels of resistance provided by the test administrator. Muscle strength is then graded based on the level of contraction that the test subject is able to elicit or maintain. Treatment then can be guided based on the determined muscle strength.

Another common assessment is the "10 Meter Walk Test" (10MWT), which is another common functional mobility measure in which a test subject walks a fixed distance (e.g., 10 meters) while timed to determine walking speed. Performing the 10MWT requires a stopwatch, a clear pathway usually marked at 0, 2, 12, and 14 meters, and a test administrator to observe the test subject, operate the stopwatch, calculate average speed, and record test results. To perform the 10MWT in a conventional manner, the test subject begins at rest (standing) and walks 14 meters and then comes back to rest. The test administrator starts and stops the stopwatch when either of the user's feet crosses the 2 meter and 12 meter markings, respectively (a 10-meter difference). The additional two meters at the beginning and end of the timed distance allows the test subject to come to speed and back to rest. The test administrator then calculates the average speed over the recorded 10 meters and manually records the results. Treatment then can be guided depending on these results.

The MMT and 10MWT are two common assessment tests for mobility impairment, and there are many others. Examples of additional assessments (without limitation) have been suggested in work being done at the Shepherd Center in Atlanta, Ga. A large list of rehabilitation measures may be found in the Rehabilitation Measures Database. Outcome measures specific to spinal cord injury may be found in the Spinal Cord Injury Research Evidence Project.

In an effort to restore some degree of legged mobility to individuals with paraplegia or other forms of mobility impairment, several lower limb orthoses have been developed. The simplest form of such devices is passive orthotics with long-leg braces that incorporate a pair of ankle-foot orthoses (AFOs) to provide support at the ankles, which are coupled with leg braces that lock the knee joints in full extension. The hips are typically stabilized by the tension in the ligaments and musculature on the anterior aspect of the pelvis. Since almost all energy for movement is provided by the upper body, these passive orthoses require considerable upper body strength and a high level of physical exertion, and provide very slow walking speeds.

The hip guidance orthosis (HGO), which is a variation on long-leg braces, incorporates hip joints that rigidly resist hip adduction and abduction, and rigid shoe plates that provide increased center of gravity elevation at toe-off, thus enabling a greater degree of forward progression per stride. Another variation on the long-leg orthosis, the reciprocating gait orthosis (RGO), incorporates a kinematic constraint that links hip flexion of one leg with hip extension of the other, typically by means of a push-pull cable assembly. As with other passive orthoses, the user leans forward against a stability aid (e.g., bracing crutches or a walker) while un-weighting the swing leg and utilizing gravity to provide hip extension of the stance leg. Since motion of the hip joints is reciprocally coupled through the reciprocating mechanism, the gravity-induced hip extension also provides contralateral hip flexion (of the swing leg), such that the stride length of gait is increased. One variation on the RGO incorporates a hydraulic-circuit-based variable coupling between the left and right hip joints. Experiments with this variation indicate improved hip kinematics with the modulated hydraulic coupling.

To decrease the high level of exertion associated with passive orthoses, the use of powered orthoses has been under development, which incorporate actuators and drive motors associated with a power supply to assist with locomotion. These powered orthoses have been shown to increase gait speed and decrease compensatory motions, relative to walking without powered assistance.

The use of powered orthoses presents an opportunity for electronic control of the orthoses. Exoskeleton devices to date, however, have lacked comprehensive control systems that also are user-friendly to maximize the effectiveness and comfort for a legged mobility exoskeleton device. Examples of powered orthoses are known. WO/2010/044087, US 2010/0094188, and U.S. Pat. No. 8,096,965 disclose a powered exoskeleton bracing system/exoskeleton bracing system. These prior art devices, however, have been insufficient for comprehensive and user-friendly control of the exoskeleton device. There have been attempts to provide at least generalized control of an exoskeleton device, including the providing of safety indications. For example, U.S. Pat. No. 8,905,955 B2 discloses a method of controlling an exoskeleton bracing system comprising halting actuation of the motorized joints when a signal that is received from a tilt sensor indicates falling. These methods are described entirely within the context of standing and sitting transitions.

WO/2013/142777 discloses a method of controlling a powered lower extremity orthotic, wherein the leg support includes a thigh segment, shank segment, further comprising estimating an angle of the shank segment with respect to vertical. The device is control to take a step when the shank angle exceeds a threshold with respect to gravity, and the system further comprises signaling the user when placing the orthotic into a state corresponding to taking a step, the signal generally being accomplished by an auditory tone, haptic vibration, or visual cue. WO/2013/142777 also discloses a related method of controlling a powered lower extremity orthotic, wherein the leg support includes a thigh segment, shank segment. The method comprises estimating an angle of the shank segment with respect to vertical, and the device takes a step when the shank angle exceeds a threshold with respect to gravity. The method further comprises calculating a center of pressure average trajectory over time, calculating the variation of that location over time, and generating a proficiency score. The method further comprises restricting which exoskeleton states may be reached based on at least a threshold of said amount of variation.

WO/2014/159577 discloses a lower extremity orthosis configured to be coupled to a person, and a controller that receives signals from a plurality of sensors. The controller estimates at least one feedback ready value based on the sensor output, and at least one feedback system operated by the controller is configured to communicate the feedback ready value to the user. The orthosis provides the user with orthosis operational information not otherwise available to the user, wherein the feedback systems include at least one light indicating actuator effort, a plurality of lights proportionally indicating actuator torque, at least one light indicating force at an interface point, a plurality of lights proportionally indicating force at an interface point. The feedback ready value is selected from: force between user and orthosis, effort applied by orthosis, torque applied by orthosis, maximum effort applied over gait cycle, average effort applied over gait cycle, center of pressure, limb position, center of mass position, foot clearance, orthosis state, next orthosis action, optimal gain aid orientation, and movement of the person.

Although the above conventional control systems provide a certain level of control, the scope of control is directed principally for the purpose of compensating for a given impairment. Related safety features also may be provided. Such control systems for exoskeleton devices and other mobility assistance devices to date have lacked comprehensiveness in a manner that is user-friendly to maximize the effectiveness for enhanced user performance and physical improvement. Modern technological advances have allowed for the development of mobility assistance devices which provide increased capability and independence to the individuals who use them. This is especially meaningful for individuals who utilize mobility assistance devices to overcome impairments resulting from injury, disability, or disease. As such devices become increasingly mobile with more advanced control, with numerous sensors, actuators, and interfaces, the traditional role of assistance devices primarily or solely for compensating for impairment represents a limited use of such devices. Accordingly, current devices are not being utilized to their full potential.

SUMMARY OF THE INVENTION

The present invention is directed to control systems for automated assessment and adjustment of components of a mobility assistance device, such as a legged mobility device or "exoskeleton" device. The control systems of the present invention operate to leverage device sensors, actuators, and interfaces to perform automated assessment of user impairment and/or make automated adjustments to the state and/or operation of the device components to improve assessment outcomes.

As referenced above, as mobility assistance devices have become increasingly mobile with more advanced control, with numerous sensors, actuators, and interfaces, the traditional role of assistance devices primarily or solely for compensating for impairment represents a limited use of such devices. The scope of usefulness of such devices, therefore, has tremendous potential to broaden. Rather than simply compensating for impairment, mobility assistance devices in accordance with the present invention perform automated assessment of the individual user and device, and then may perform automated adjustment of device component state and/or operation to enhance the user's recovery or physical capability. By providing for automated assessment and adjustment of the mobility assistance device, there is reduced need for specialized equipment, expert personnel, and additional external equipment for assessment and adjustment, while allowing the mobility assistance device to play a broader role in the management of impairments for which the device traditionally has only compensated. In other words, in addition to the traditional role of compensating for impairment, the mobility assistance device of the present invention can improve and optimize user performance through automated assessment and adjustment of the mobility assistance device.

In exemplary embodiments, the mobility assistance device is a legged mobility device, or "exoskeleton" device. A control system within the device may perform an automated assessment of muscle strength and may adjust the device level of assistance accordingly. Such an exoskeleton device would be worn by an individual who requires assistance to compensate for reduced mobility due to lower extremity weakness. To determine how much assistance the exoskeleton device should provide, the device control system may operate to control device instrumentation, actuation, and control logic to perform standard muscle assessment tests automatically. Automated assessments may include, for example, automated performance of the Manual Muscle Test (MMT) or 10-Meter Walk Test (10MWT), although other assessments may be automated. The control system of the exoskeleton device may then analyze the motion that was achieved during the assessment to determine a muscle grade and in turn determine an assistance level that the device components, and particularly the joint components, should provide. The control system may then automatically adjust the device components in accordance with the determined assistance level. The control system further may operate to prompt the user to participate in subsequent tests to assess the effectiveness of that assistance level and adjust the assistance level accordingly.

Aspects of the present invention may include a mobility assistance device having a control system that is configured to: perform automated assessment of a user performance; and execute automated adjustments to device component state and/or operation based on the automated assessment to enhance the user's recovery or physical capability. This automated assessment and adjustment reduces the need for specialized facilities, expert personnel, or additional external equipment. Such automation is achieved by the control system's integration of specific information related to the mobility assistance device, the impairments for which the device compensates, and information pertaining to specific user characteristics. With such integration, the device may act as an aid to diagnose and treat an impairment, in addition to simply performing the traditional role of compensating for an impairment. The usefulness of the present invention, therefore, goes substantially beyond the limited functions that have been traditionally performed by conventional mobility assistance devices.

A method of controlling a mobility device and a related mobility device including at least one drive component that drives at least one joint component are described. The control method may include executing a control application with an electronic controller to perform steps including: receiving a command in the control system of the mobility device for initiating an automated assessment and adjustment protocol; controlling one or more mobility device components to perform the automated assessment; electronically gathering user performance data associated with the automated assessment and determining user performance metrics; and electronically controlling one or more of the mobility device components in accordance with the performance metrics. The automated assessment may include controlling mobility device components to perform a predetermined assessment activity related to performance of the mobility device and/or user. The automated assessment may be any predetermined assessment in existence or that may be developed in the future as technology and medical progress advances. Examples without limitation include an automated MMT or 10MWT. Automatic adjustments to the device components, including adjusting tension and resistance levels of the joint components, may then be made based on the performance metrics gathered from the automated assessment.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION

Figure 1:
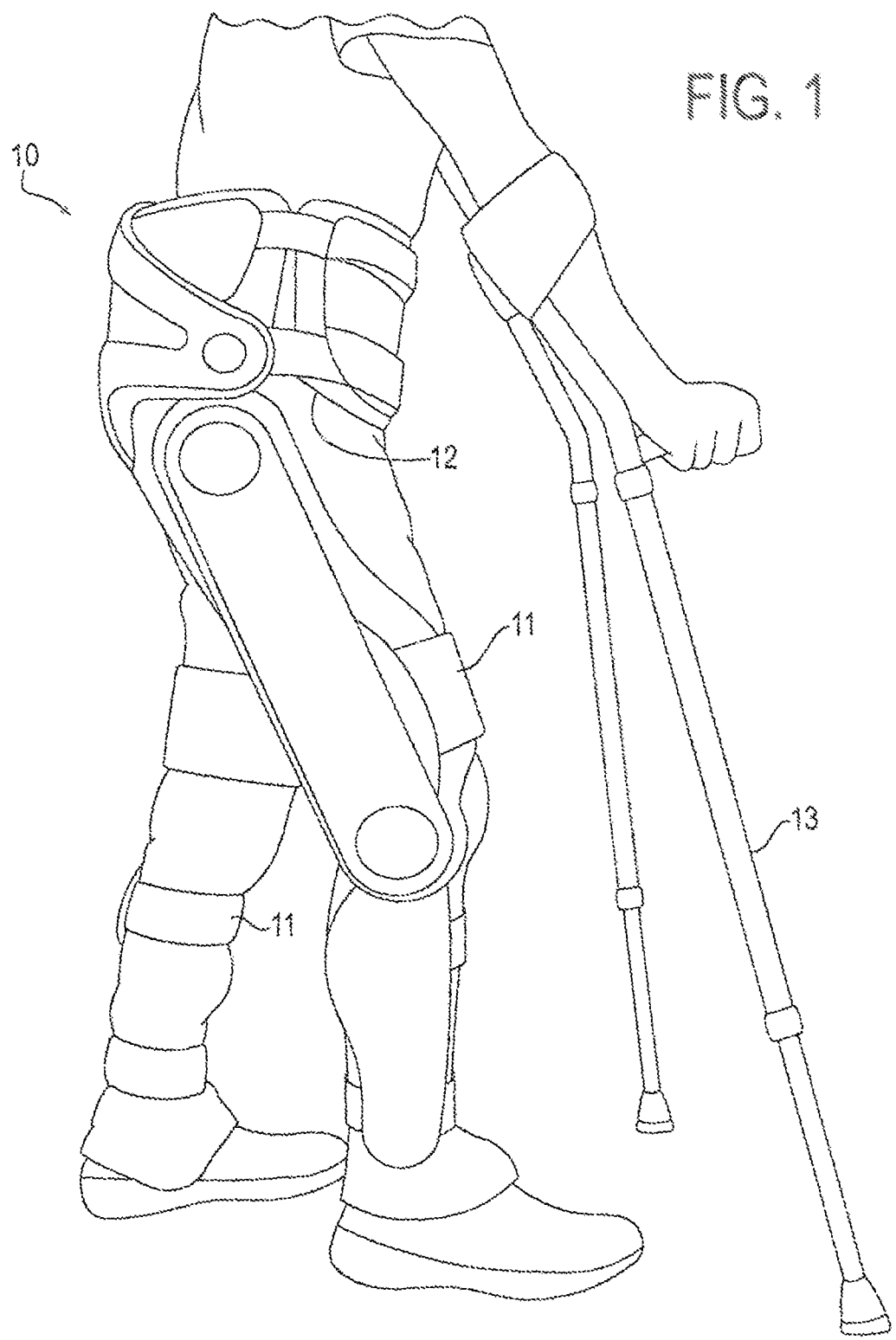
FIG. 1 is a drawing depicting an exemplary exoskeleton device as being worn by a user.

Embodiments of the present invention will now be described with reference to the drawings, wherein like reference numerals are used to refer to like elements throughout. It will be understood that the figures are not necessarily to scale.

For context, FIGS. 1-13 depict various views of an exemplary exoskeleton device that may be used in connection with the control system and methods of the present invention. A somewhat generalized description of such exoskeleton device is provided here for illustration purposes. A more detailed description of such device may be found in Applicant's International Patent Appl. No. PCT/US2015/023624 filed on Mar. 3, 2015, which is incorporated here in its entirety by reference. It will be appreciated, however, that the described exoskeleton device presents an example usage, and that the control system and methods of the present invention are not limited to any particular configuration of an exoskeleton device. Variations may be made to the exoskeleton device, while the features of the present invention remain applicable. In addition, the principles of this invention may be applied generally to any suitable mobility device. Such mobility devices include, for example, orthotic devices which aid in mobility for persons without use or limited use of a certain body portion, and prosthetic devices, which essentially provide an electromechanical replacement of a body part that is not present such as may be used by an amputee or a person congenitally missing a body portion.

As show in FIG. 1, an exoskeleton device 10, which also may be referred to in the art as a "wearable robotic device", can be worn by a user. To attach the device to the user, the device 10 can include attachment devices 11 for attachment of the device to the user via belts, loops, straps, or the like. Furthermore, for comfort of the user, the device 10 can include padding 12 disposed along any surface likely to come into contact with the user. The device 10 can be used with a stability aid 13, such as crutches, a walker, or the like.

Figure 2:
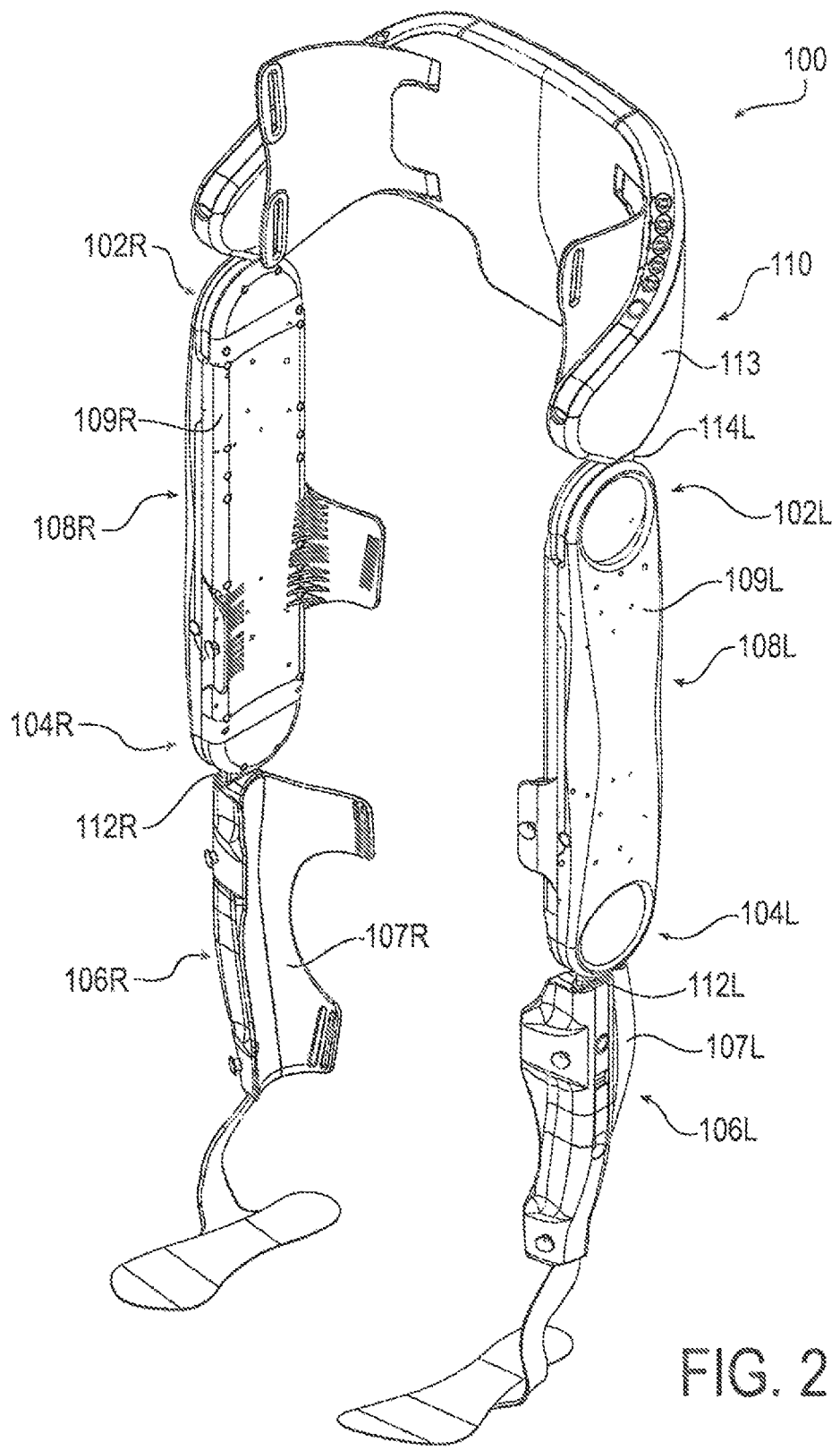
FIG. 2 is a drawing depicting a perspective view of an exemplary exoskeleton device in a standing position.
Figure 3:
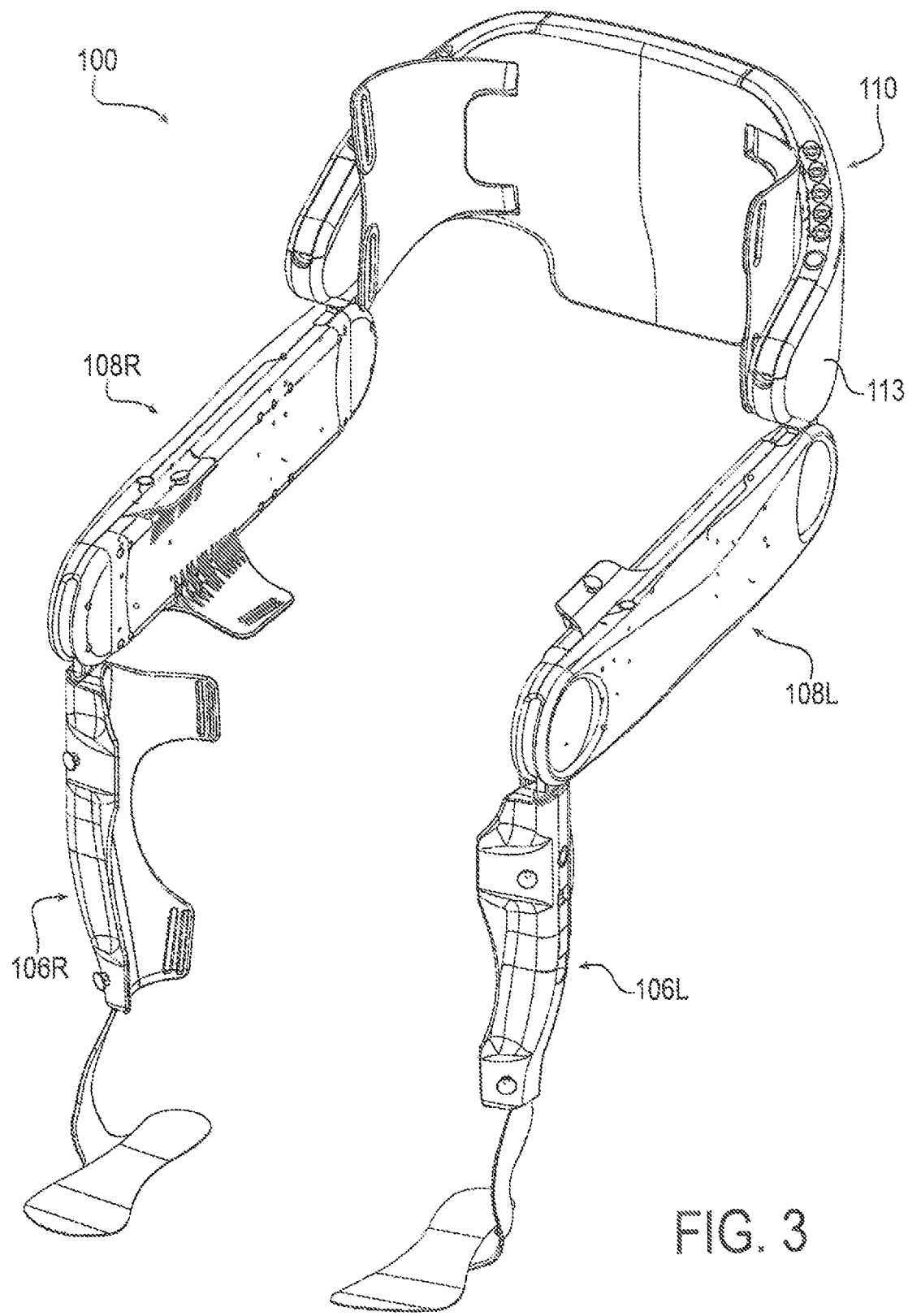
FIG. 3 is a drawing depicting a perspective view of the exemplary exoskeleton device in a seated position.
Figure 4:
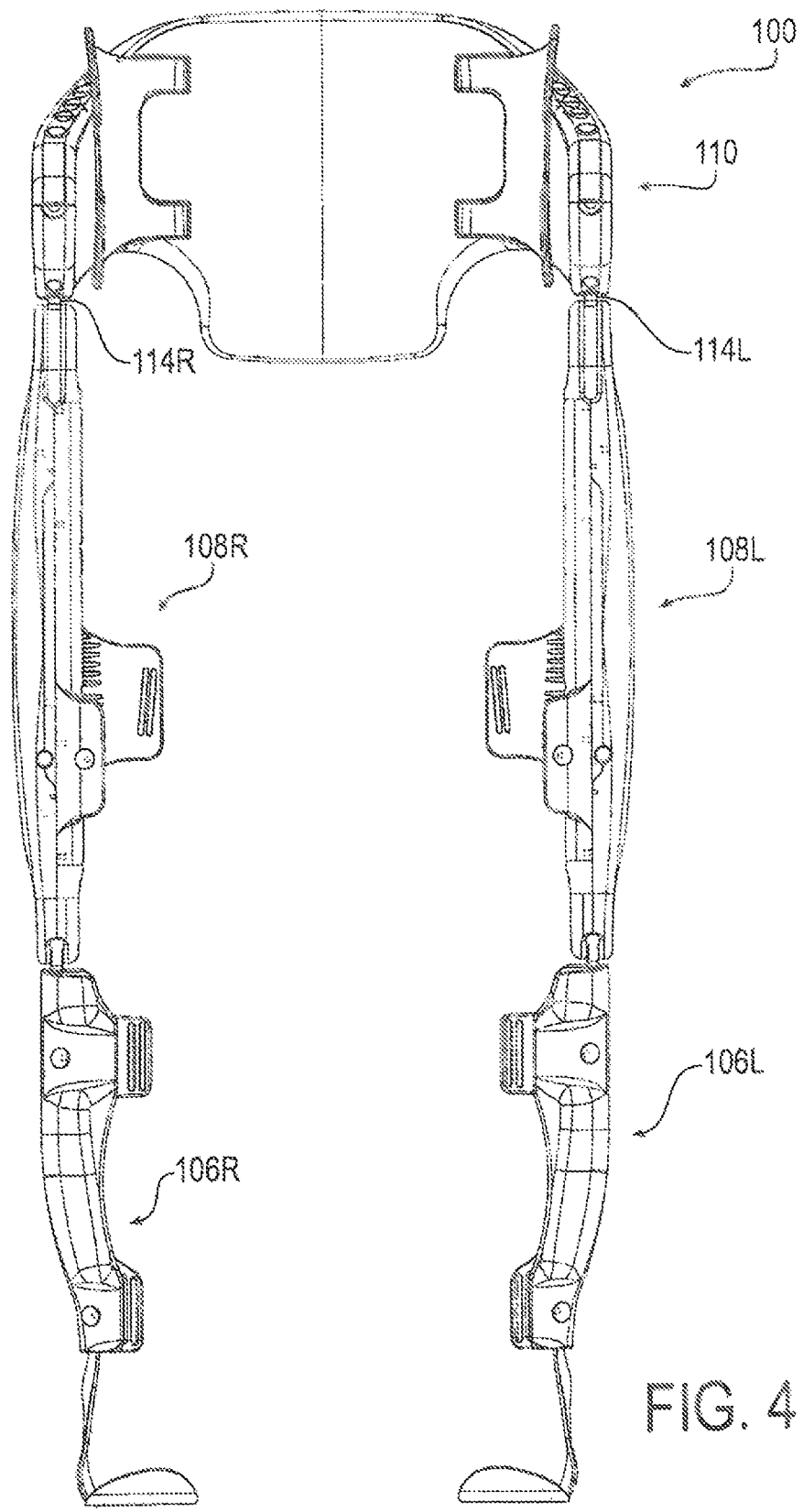
FIG. 4 is a drawing depicting a front view of the exemplary exoskeleton device in a standing position.
Figure 5:
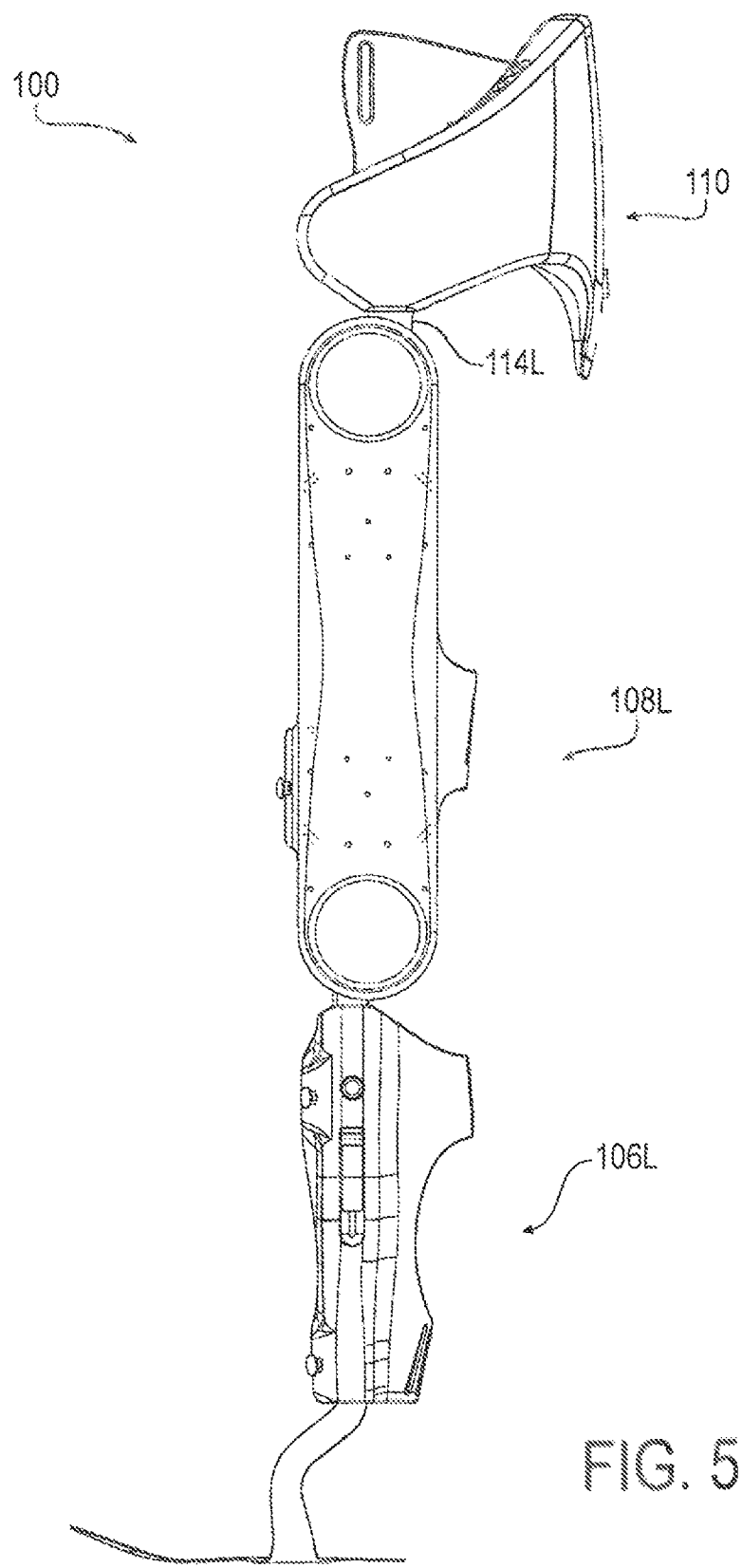
FIG. 5 is a drawing depicting a side view of the exemplary exoskeleton device in a standing position.
Figure 6:
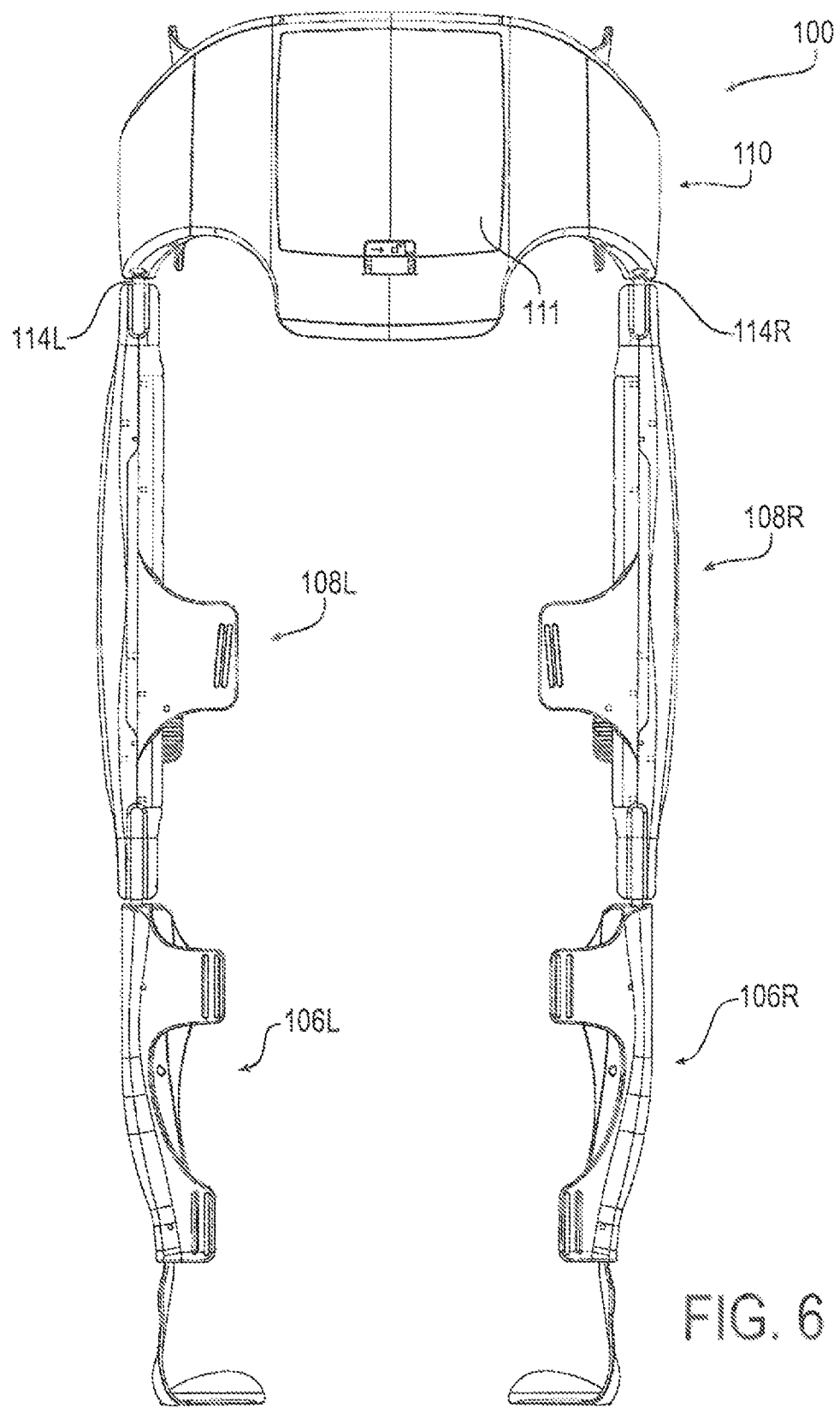
FIG. 6 is a drawing depicting a back view of the exemplary exoskeleton device in a standing position.
Figure 7:
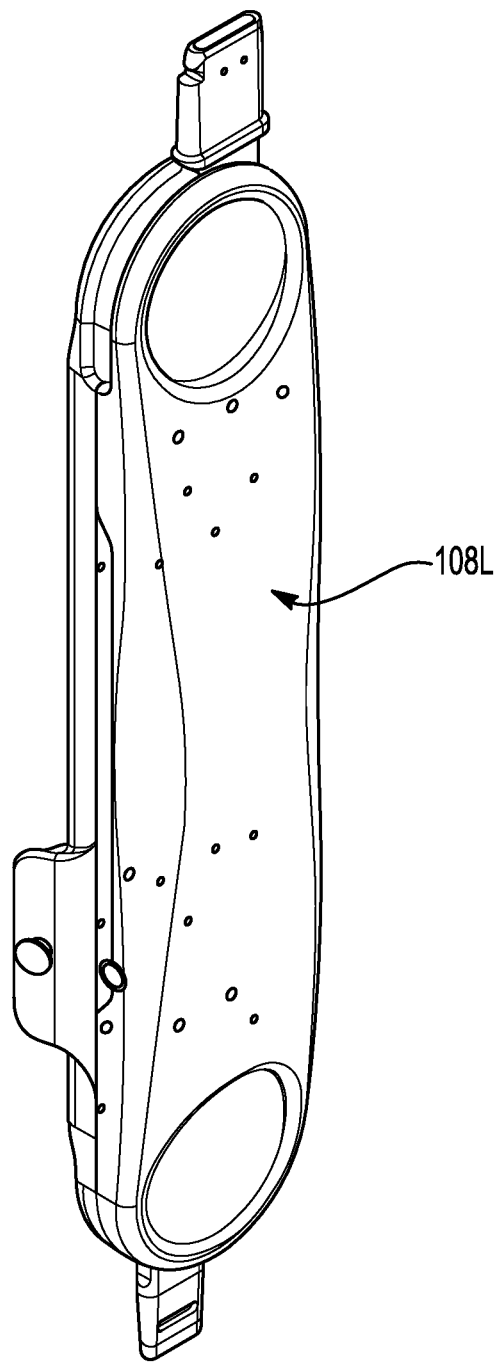
FIG. 7 is a drawing depicting a perspective view of an exemplary thigh assembly having two exemplary actuator cassettes installed therein.
Figure 8:
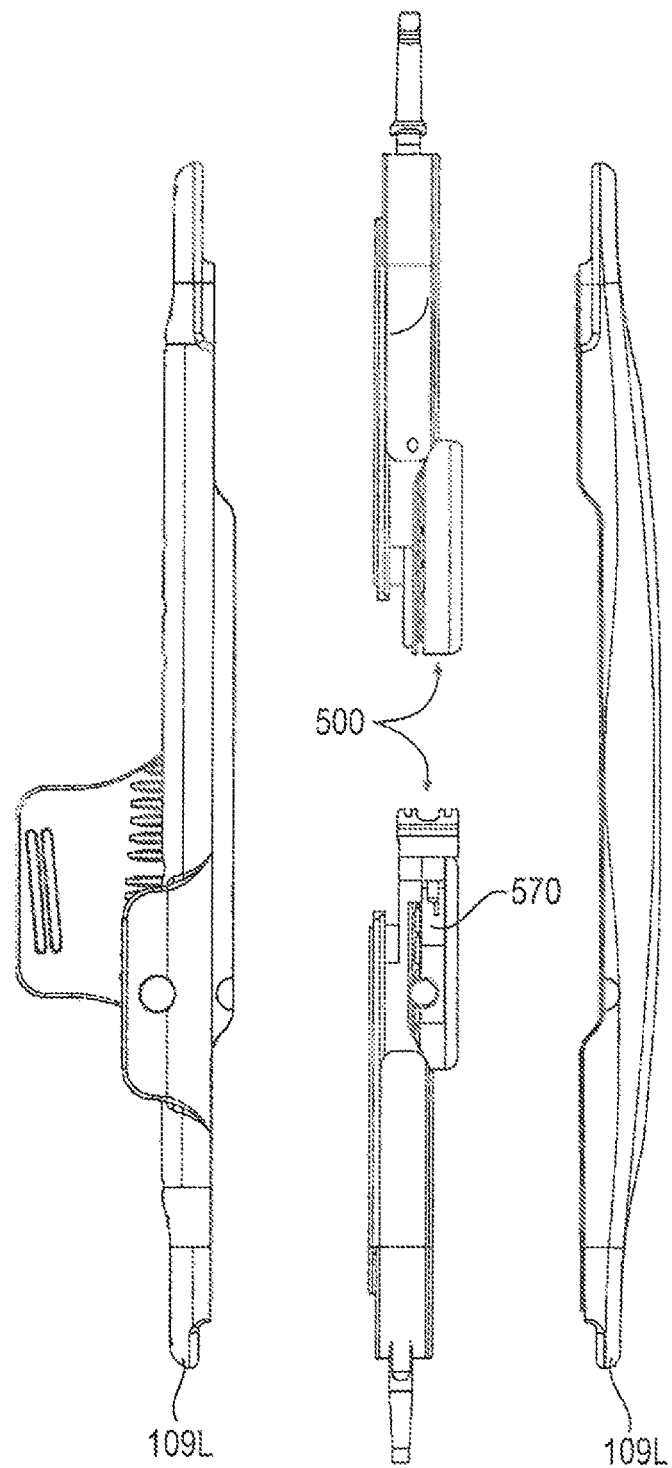
FIG. 8 is a drawing depicting a front exploded view of the exemplary thigh assembly having two exemplary actuator cassettes installed therein.
Figure 9:
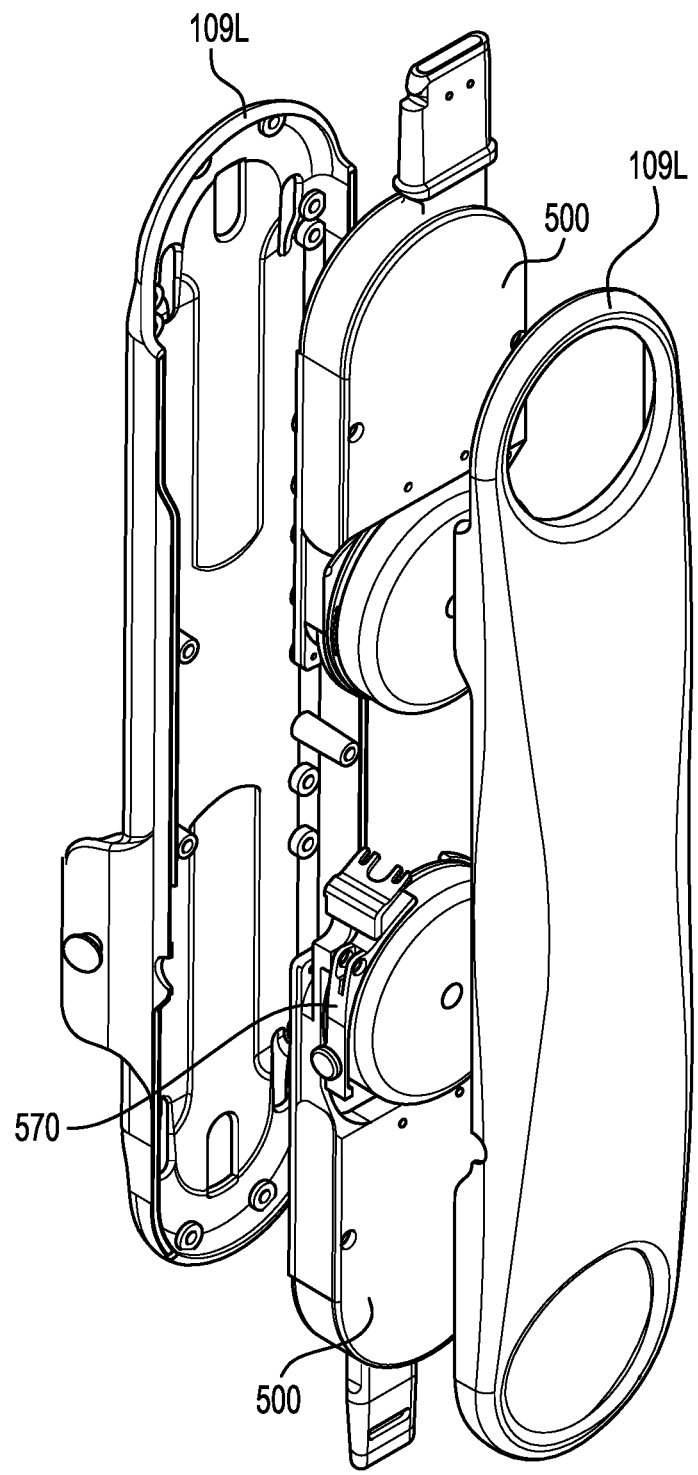
FIG. 9 is a drawing depicting a perspective exploded view of the exemplary thigh assembly having two exemplary actuator cassettes installed therein.
Figure 10:
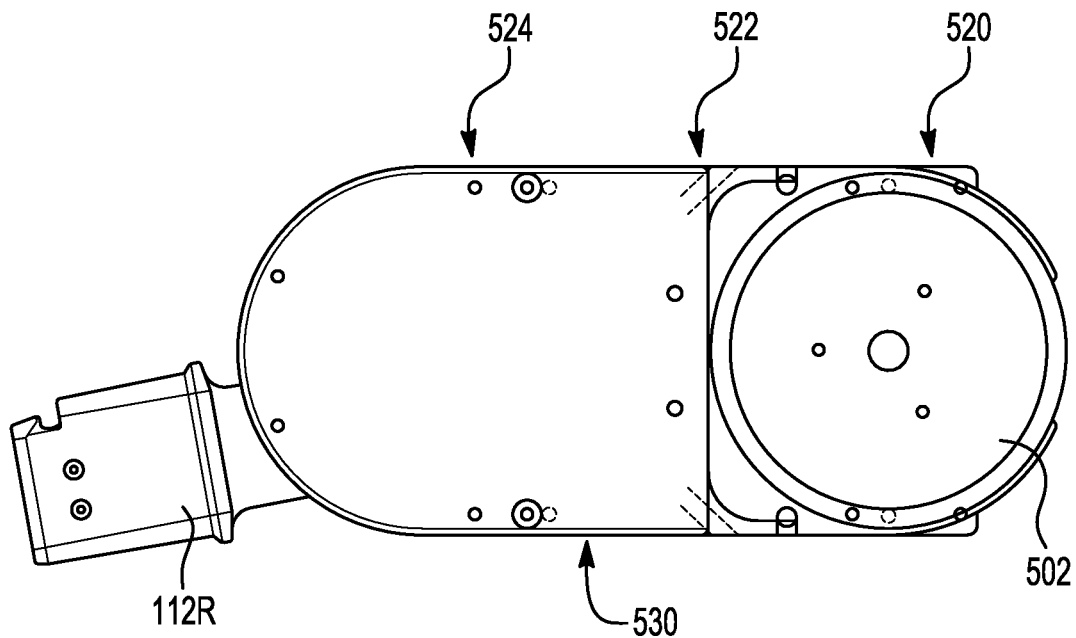
FIG. 10 is a drawing depicting a top view of an exemplary actuator cassette.
Figure 11:
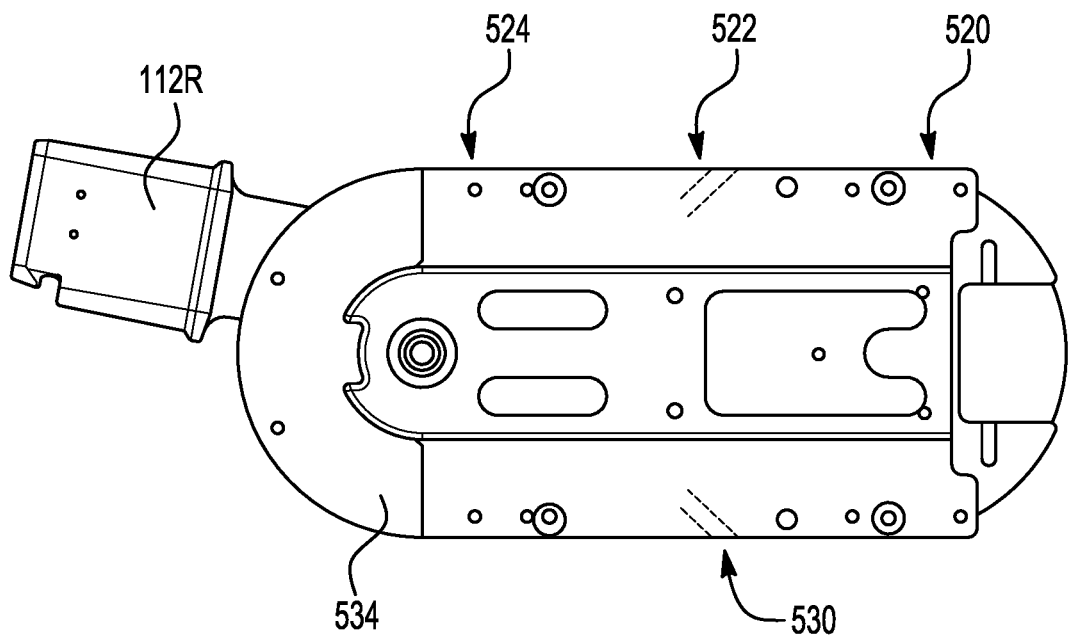
FIG. 11 is a drawing depicting a bottom view of an exemplary actuator cassette.
Figure 12:
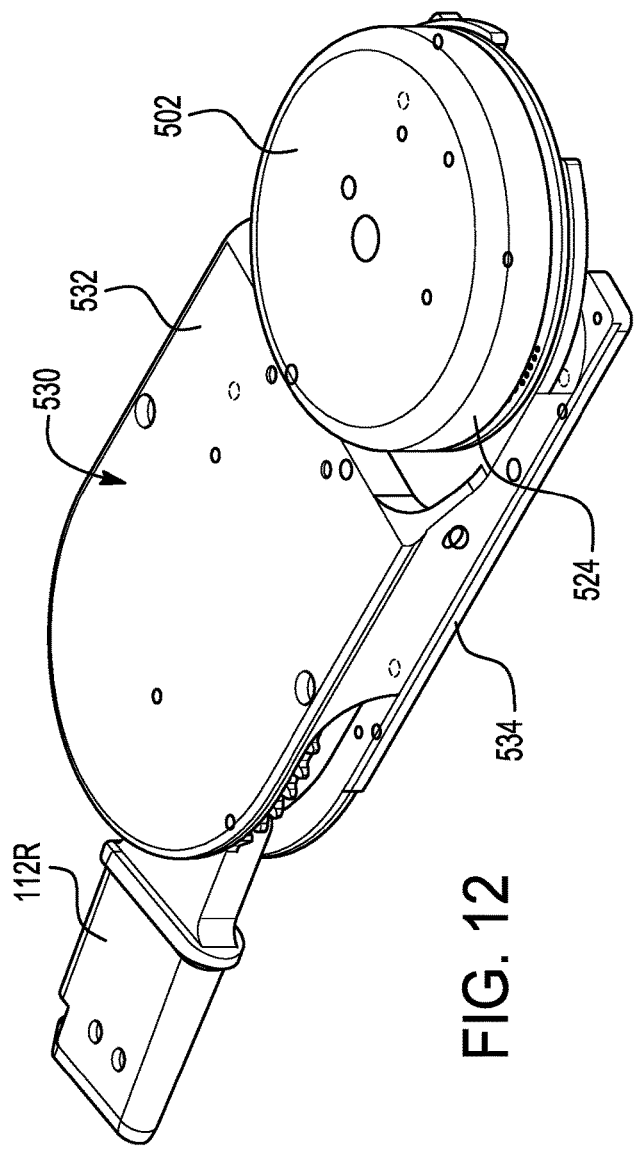
FIG. 12 is a drawing depicting a perspective view of an exemplary actuator cassette.

An exemplary legged mobility exoskeleton device is illustrated as a powered lower limb orthosis 100 in FIGS. 2-6. Specifically, the orthosis 100 shown in FIGS. 2-6 may incorporate four drive components configured as electromotive devices (for example, electric motors), which impose sagittal plane torques at each knee and hip joint components including (right and left) hip joint components 102R, 102L and knee joint components 104R, 104L. FIG. 2 shows the orthosis 100 in a standing position while FIG. 3 shows the orthosis 100 in a seated position.

As seen in the figures, the orthosis contains five assemblies or modules, although one or more of these modules may be omitted and further modules may be added (for example, arm modules), which are: two lower (right and left) leg assemblies (modules) 106R and 106L, two (left and right) thigh assemblies 108R and 108L, and one hip assembly 110. Each thigh assembly 108R and 108L includes a respective thigh assembly housing 109R and 109L, and link, connector, or coupler 112R and 112L extending from each of the knee joints 104R and 104L and configured for moving in accordance with the operation of the knee joints 104R and 104L to provide sagittal plane torque at the knee joints 104R and 104L.

The connectors 112R and 112L further may be configured for releasably mechanically coupling each of thigh assembly 108R and 108L to respective ones of the lower leg assemblies 106R and 106L. Furthermore, each thigh assembly 108R and 108L also includes a link, connector, or coupler 114R and 114L, respectively, extending from each of the hip joint components 102R and 102L and moving in accordance with the operation of the hip joint components 102R and 102L to provide sagittal plane torque at the knee joint components 104R and 104L. The connectors 114R and 114L further may be configured for releasably mechanically coupling each of thigh assemblies 108R and 108L to the hip assembly 110.

In some embodiments, the various components of device 100 can be dimensioned for the user. However, in other embodiments the components can be configured to accommodate a variety of users. For example, in some embodiments one or more extension elements can be disposed between the lower leg assemblies 106R and 106L and the thigh assemblies 108R and 108L to accommodate users with longer limbs. In other configurations, the lengths of the two lower leg assemblies 106R and 106L, two thigh assemblies 108R and 108L, and one hip assembly 110 can be adjustable. That is, thigh assembly housings 109R, 109L, the lower leg assembly housings 107R and 107L for the lower leg assemblies 106R, 106L, respectively, and the hip assembly housing 113 for the hip assembly 110 can be configured to allow the user or medical professional to adjust the length of these components in the field. For example, these components can include slidable or movable sections that can be held in one or more positions using screws, clips, or any other types of fasteners. In view of the foregoing, the two lower leg assemblies 106R and 106L, two thigh assemblies 108R and 108L, and one hip assembly 110 can form a modular system allowing for one or more of the components of the orthosis 100 to be selectively replaced and for allowing an orthosis to be created for a user without requiring customized components. Such modularity can also greatly facilitate the procedure for donning and doffing the device.

In orthosis 100, each thigh assembly housing 109R, 109L may include substantially all the drive components for operating and driving corresponding ones of the knee joint components 104R, 104L and the hip joint components 102R, 102L. In particular, each of thigh assembly housings 109R, 109L may include drive components configured as two motive devices (e.g., electric motors) which are used to drive the hip and knee joint component articulations. However, the various embodiments are not limited in this regard, and some drive components can be located in the hip assembly 110 and/or the lower leg assemblies 106R, 106L.

A battery 111 for providing power to the orthosis can be located within hip assembly housing 113 and connectors 114R and 114L can also provide means for connecting the battery 111 to any drive components within either of thigh assemblies 108R and 108L. For example, the connectors 114R and 114L can include wires, contacts, or any other types of electrical elements for electrically connecting battery 111 to electrically powered components in thigh assemblies 108R and 108L. In the various embodiments, the placement of battery 111 is not limited to being within hip assembly housing 113. Rather, the battery can be one or more batteries located within any of the assemblies of orthosis 100.

The referenced drive components may incorporate suitable sensors and related internal electronic controller or control devices for use in control of the exoskeleton device. Such internal control devices may perform using the sensory information the detection of postural cues, by which the internal control device will automatically cause the exoskeleton device to enter generalized modes of operation, such as sitting, standing, walking, variable assist operation, and transitions between these generalized modes or states (e.g., Sit to Stand, Stand to Walk, Walk to Stand, Stand to Sit, etc.) and step transition (e.g., Right Step, Left Step). The internal electronic control devices further may perform fall mitigation and recovery operations for the exoskeleton device, as described for example in Applicant's International Patent Appl. No. PCT/US2016/016319 filed on Feb. 3, 2016, which is incorporated here in its entirety by reference.

The internal electronic control devices and related electronics further may incorporate or include a mobility assistance device communications interface that is configured to transmit and receive signals over an electronic signal interface. In exemplary embodiments, the mobility device communications interface may communicate electronically over a wireless interface by transmitting signals to and receiving signals from a communications interface of an electronic communication device including a control application for controlling the drive components of the mobility device.

To perform such operations, the drive systems and internal control device of the mobility assistance device may employ the use of accelerometers, gyroscopes, inertial measurement, and other sensors to detect and observe the upper leg orientation or angle and angular velocity. The internal control device may then selectively control the drive components to modulate the joint components, and particularly the knee and hip joint components, to apply torque, implement locked or released states, or otherwise effect positioning or movement of the joint components control of the exoskeleton device for mode operation or for fall mitigation.

To implement the features of the present invention, the exoskeleton device or other mobility device may include a control system having one or more processor devices that are configured to execute program code stored on a non-transitory computer readable medium embodying the control methods associated with the generalized control of the exoskeleton device, including the control operations of the present invention. It will be apparent to a person having ordinary skill in the art of computer programming of electronic devices how to program the electronic control device to operate and carry out logical functions associated with present invention. Accordingly, details as to specific programming code have been left out for the sake of brevity. Also, controller functionality could be carried out via dedicated hardware, firmware, software, or any combinations thereof, without departing from the scope of the invention. As will be understood by one of ordinary skill in the art, therefore, the control system may have various implementations. For example, the control system may be configured as any suitable processor device, such as a programmable circuit, integrated circuit, memory and I/O circuits, an application specific integrated circuit, microcontroller, complex programmable logic device, other programmable circuits, or the like. The control system may also include a non-transitory computer readable medium, such as random access memory (RAM), a read-only memory (ROM), an erasable programmable read-only memory (EPROM or Flash memory), or any other suitable medium. Instructions for performing the methods described below may be stored in the non-transitory computer readable medium and executed by the processor device.

In the various embodiments, to maintain a low weight for orthosis and a reduced profile for the various components, the drive components may include a substantially planar drive system that is used to drive the hip and knee articulations of the joint components. For example, each motor can respectively drive an associated joint component through a speed-reduction transmission using an arrangement of sprocket gears and chains substantially parallel to the plane of sagittal motion. Referring to FIGS. 7-13, consolidating the moveable parts into self-contained units, referred to herein as "cassettes," allow for ease of maintenance and replacement because cassettes are swappable, making them easier to service or requiring less of a variety in spare components. As used herein, "self-contained" means that the cassette includes everything necessary to operate in a fully functional manner if supplied with power. Thus, for example, if power is supplied to electrical contacts of the cassette, the cassette would actuate.

In the illustrated embodiment of the drive components, the motor is integrated onto a common baseplate along with sprockets that control the motion of a joint link. Bearings and chains, with and/or without tensioners provide smooth and efficient transfer of motion from the motor to the joint angle. Integrating the motor into the cassette allows for a thinner overall package configuration and provides consistent alignment among parts. Moreover, integrating the motor also creates a larger surface area to transfer and emit heat generated by the motor. In the instance of a mobility assistance device, these cassettes may pertain to a specific joint or set of joints on the device. Each may have a unique actuation unit or share an actuation unit. They may include actuators, with or without a power source, and/or a method of transmitting movement. The illustrated embodiment includes a brushless DC motor with chains and sprockets to create and transmit motion, although other embodiments may utilize electric motors, linear actuators, piezoelectric actuators, belts, ball screws, harmonic drive, gear drive (bevel or planetary), or any combination thereof. The cassettes may also house the electronic control device, and further may contain the referenced sensor elements such as the accelerometers, gyroscopes, inertial measurement, and other sensors to detect and observe the upper leg orientation or angle and angular velocity. The self-contained cassette units can be preassembled to aid in manufacturing the broader device. This allows for quick servicing of the device since individual cassettes can be swapped out and serviced.

Therefore, a removable, self-contained, ovular actuator cassette 500 may be receivable in a receptacle of a wearable robotic device. The cassette 500 may include a first circular portion 520 housing a motive device (e.g., an electric motor) 502. A second circular portion 522 may be longitudinally offset and longitudinally overlapping the first circular portion and may house a first portion of a drivetrain 514, 516 operatively coupled to and driven by the motive device 502. A third circular portion 524 may be longitudinally offset from the first and second circular portions and longitudinally overlapping the second circular portion and may house a second portion of the drivetrain 504. These three overlapping circular portions make an ovular shape, which may include the referenced sensors and electronic control devices. Therefore, an ovular housing 530 may support the motive device 502 and drivetrain 502, 514, 516. Long sides of the ovular housing are straight and parallel with each other and tangentially terminate as curved end surfaces of the ovular housing.

Figure 13:
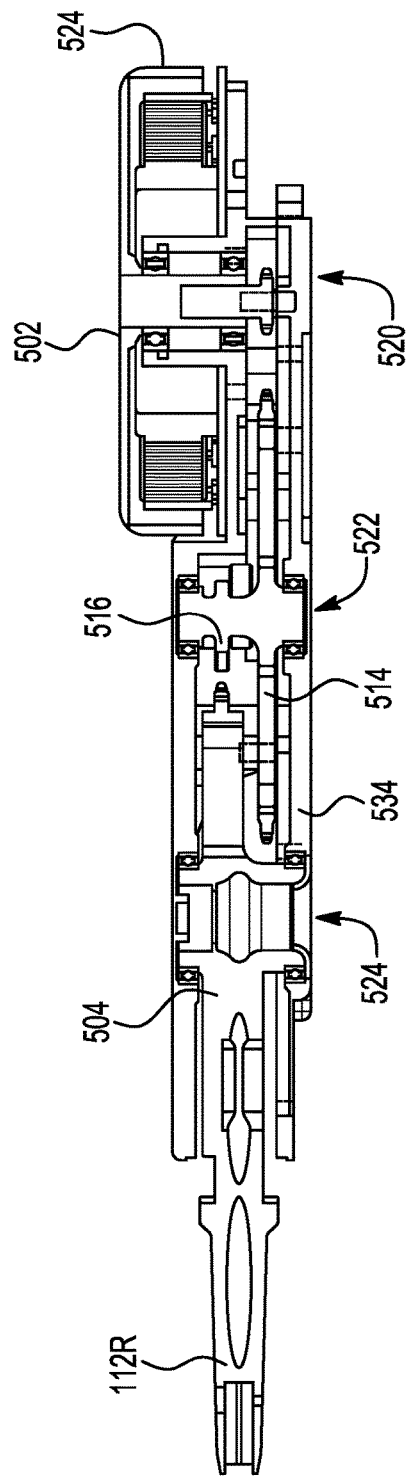
FIG. 13 is a drawing depicting a cross-sectional view of an exemplary actuator cassette taken along the longitudinal direction.

Referring to FIGS. 7-13, with FIG. 13 of the right side being representative, the powered joints may be implemented by disposing a joint sprocket gear 504 at one end of thigh assembly housing 109R parallel to the sagittal plane and configuring the joint sprocket gear 504 to rotate parallel to the sagittal plane. To provide the sagittal plane torque for knee joint component 102R, the connector 112R can extend from the joint sprocket gear 504 and be mechanically connected, so that rotation of the joint sprocket gear 504 results in application of torque to the lower leg assembly 106. A slot or receiving element can be provided for the connector 112R to link the thigh assembly 108R and lower leg assembly 106R. The receiving element and the connector 112R can be configured such that the connector can removably connect the thigh assembly 108R and lower leg assembly 106R. In the various embodiments, clips, screws, or any other types of fastener arrangements can be used to provide a permanent or a removable connection. In some embodiments, quick connect or "snap-in" devices can be provided for providing the connection. That is, these quick connect devices allow connections to be made without the need of tools. These types of quick connect devices can not only be used for mechanically coupling, but for electrical coupling with the sensors and control electronics. In some embodiments, a single quick connect device can be used to provide both electrical and mechanical coupling. However, the various embodiments are not limited in this regard and separate quick connect devices can be provided for the electrical and mechanical coupling. It is worth noting that with quick disconnect devices at each joint, the orthosis can be easily separated into three or five modular components—right thigh, left thigh, right lower leg, left lower leg, and hip assemblies—for ease of donning and doffing and also for increased portability.

The knee joint component 104R may be actuated via operation of a motor 502, as discussed above. The motor 502 can be an electric motor that drives the knee joint 104R (i.e., joint sprocket gear 504) using a two-stage chain drive transmission. For example, as shown in FIG. 13, a first stage can include the motor 502 driving, either directly or via a first chain, a first drive sprocket gear 514. The first drive sprocket gear 514 is mechanically coupled to a second drive sprocket gear 516 so that they rotate together about the same axis based on the power applied by motor 502 to first drive sprocket gear 514. The second drive sprocket gear 516 can be arranged so that it is disposed in the same plane as the joint gear 504. Thus, a second chain can then be used to drive joint sprocket gear 504 using the second drive sprocket gear 516 and actuate the knee joint 104R. The gear ratios for the various components described above can be selected based on a needed amount of torque for a joint, power constraints, and space constraints.

Each stage of the chain drive transmission can include tensioners, which can remove slack from a chain and mitigate shock loading. Such tensioners can be adjustable or spring loaded. In addition, a brake 570 can be provided for motor 502. For example, a solenoid brake may be provided which engages a brake pad against the rotor 524 of the motor 502 in one state, and disengages the brake pad in another state. However, the various embodiments are not limited to this particular brake arrangement and any other methods for providing a brake for motor 502 can be used without limitation.

The configuration illustrated in FIG. 13 has been discussed above with respect to an arrangement of sprocket gears and chains. However, the various embodiments are not limited in this regard. That is, any other arrangement of gears, with or without chains, and providing a reduced profile can be used. Furthermore, the various embodiments disclosed herein are not limited to an arrangement of gears and/or chains. For example, in some configurations, a belt and pulley arrangement could be used in place of the chain and sprocket arrangement. Furthermore, a friction drive arrangement can also be used. Also, any combination of the arrangements discussed above can be used as well. Additionally, different joints can employ different arrangements.

In the various embodiments of the drive components, a motor for each of the hip and knee joint components 102R, 102L, 104R, 104L can be configured to provide a baseline amount of continuous torque and a higher amount of torque for shorter periods of time. For example, in one configuration, at least 10 Nm of continuous torque and at least 25 Nm of torque for shorter (i.e., 2-sec) durations are provided. In another example, up to 12 Nm of continuous torque and 40 Nm of torque for shorter (i.e., 2-sec) durations. As a safety measure, both knee joints 104R and 104L can include normally locked brakes, as discussed above, in order to preclude knee buckling in the event of a power failure.

Figure 14:
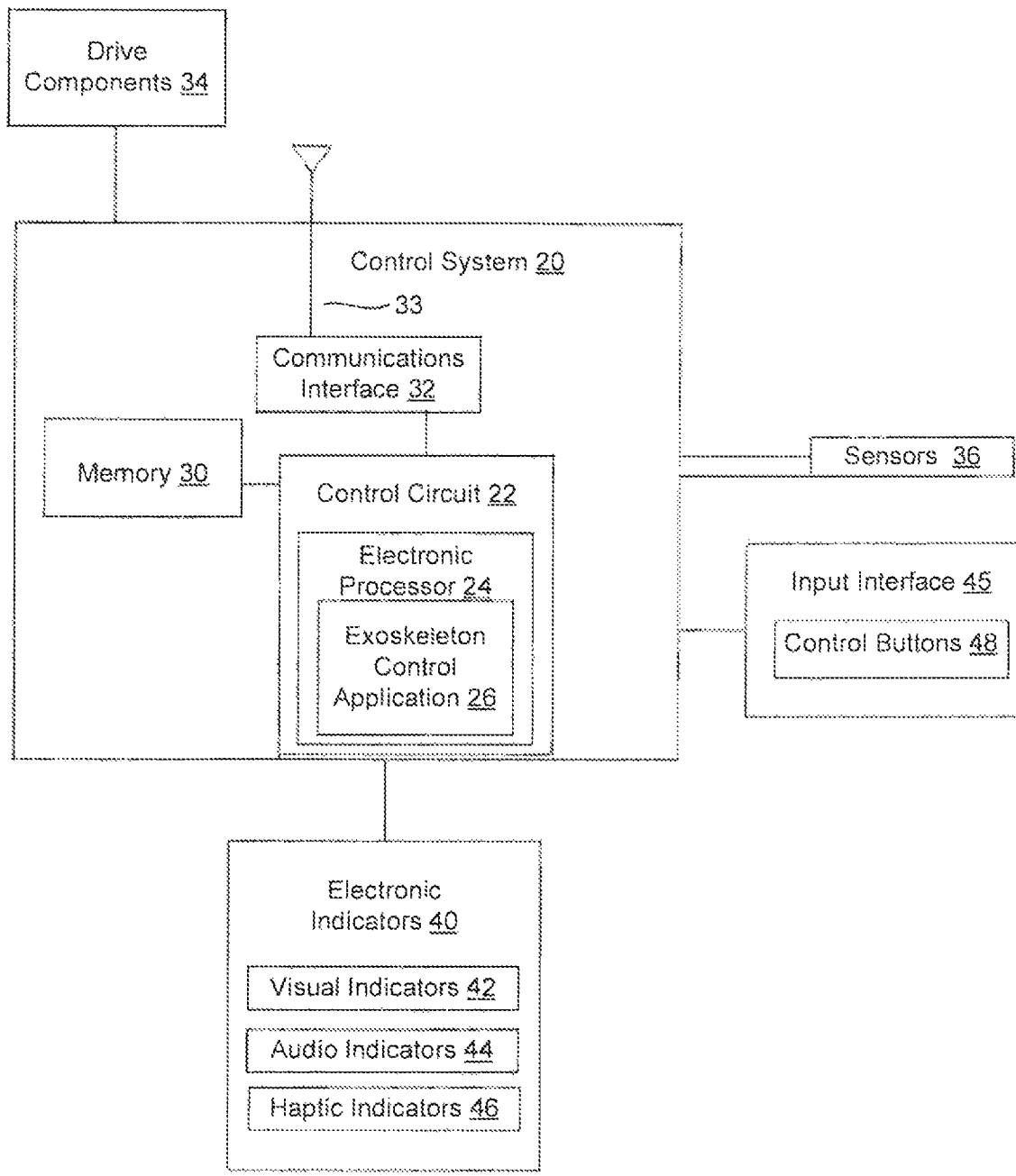
FIG. 14 is a drawing depicting a schematic block diagram of operative portions of an exemplary control system and related electronic components of a mobility device in accordance with embodiments of the present invention.

FIG. 14 is a drawing depicting a schematic block diagram of operative portions of an exemplary control system 20 and related electronic components in accordance with embodiments of the present invention, that is a component of the mobility assistance device such as the exoskeleton device of the previous figures. The control system 20 may include a primary control circuit 22 that is configured to carry out various control operations relating to control of the exoskeleton device. The control circuit 22 may include an electronic processor 24, such as a CPU, microcontroller or microprocessor. Among their functions, to implement the features of the present invention, the control circuit 22 and/or electronic processor 24 may comprise an electronic controller that may execute program code embodied as the exoskeleton control application 26. It will be apparent to a person having ordinary skill in the art of computer programming, and specifically in application programming for electronic and communication devices, how to program the device to operate and carry out logical functions associated with application 26. Accordingly, details as to specific programming code have been left out for the sake of brevity.

The exoskeleton control application 26 may be stored in a non-transitory computer readable medium, such as random access memory (RAM), a read-only memory (ROM), an erasable programmable read-only memory (EPROM or Flash memory), or any other suitable medium. In the example of FIG. 14, the exoskeleton control application 26 is shown as being stored internally within the processing components, but the application also may be stored in an additional memory device such as the memory 30. Instructions for performing the methods described below that are stored in the non-transitory computer readable medium may be executed by the processor components 22 and 24. Also, while the code may be executed by control circuit 22 or processor 24 in accordance with an exemplary embodiment, such controller functionality could also be carried out via dedicated hardware, firmware, software, or combinations thereof, without departing from the scope of the invention.

The control system 20 may constitute internal electronic control devices and related electronics incorporated into one or more of the exoskeleton device components, and typically may be incorporated into one or more of the thigh assembly or hip assembly. The control system 20 further may include a communications interface 32 for electronic communication with components external to the control system. For example, the communications interface may provide for electronic communication via an antenna 33 with an external mobile communication device, and thus may be configured to transmit and receive signals over an electronic signal interface. In exemplary embodiments, the communications interface may communicate electronically with an external mobile communication device over a wireless interface by transmitting signals to and receiving signals from the drive components for control of the mobility device. A mobile communications device and related control systems and methods are disclosed Applicant's International Patent Appl. No. PCT/US2016/40304 filed on Jun. 30, 2016, which is incorporated here in its entirety by reference.

The control system 20 further may be in electronic communication with both sensory and drive components of the exoskeleton device. The connections may be hard wired connections via internal circuit boards and other wired connections, but wireless communication also may be employed between the control system and/or sensor and drive components. In FIG. 14 the drive components (which are described in detail above) are generally indicated by block 34, and the sensors are generally indicated by block 36. For gathering appropriate sensory information, the sensors 36 may include the use of accelerometers, gyroscopes, inertial measurement, and other sensors to detect and observe the upper leg and torso orientation or angle and angular velocity. Example sensors may include hall effect sensors, magnetic angle sensors, accelerometer sensors, gyroscope sensors, resistance temperature detectors, and others. There also may be one or more redundant sensors that correspond respectively to one or more of the above sensors, and the redundant sensors may provide sensor information when there is a sensor fault detected in a respective sensor.

The control system 20 may then selectively control the drive components 34 to configure and modulate the joint components of the exoskeleton device, and particularly the knee and hip joint components, to apply torque, implement locked or released states, or otherwise effect positioning or movement of the joint components control of the exoskeleton device for various modes of operation and for fall mitigation.

As described for example in Applicant's referenced previous patent applications, in the described exoskeleton device operation generally is automated based on sensory detections. As an example, to go from sit to stand a user may pull in the legs and lean forward, as any person normally does when getting ready to stand. Upon sensing such a pre-standing position, the exoskeleton drive system would send a haptic feedback signal to the user, such as a vibration indicator, informing the user that a transition to standing will occur. Control of mobility mode of operation (sit, stand, walk, etc.), and transitions between mobility modes, proceeds as warranted. Mode transitions and mode operation, therefore, is operated generally by the sensors reading user postural cues, which are interpreted by the control system that in turn generates control signals to drive operation of the drive components.

The control system 20 further may be in electronic communication with a plurality of electronic indicators 40. In FIG. 14, the electronic indicators are generally indicated by block 40. The electronic indicators may include visual indicators 42 that indicate aspects of device state and operation by lighting. In exemplary embodiments, the lighting may be color-coded lighting in which light emitting diodes (LEDs) are employed as the visual indicators. The electronic indicators further may include audio indicators 44, by which speakers may be employed to provide audio alerts pertaining to aspects of device state and operation. Different sounds may be employed for different types of audio alerts, and may be used in combination with the visual indicators 42 to provide multiple indicator combinations corresponding to information pertaining to different aspects of device state and operation. The electronic indicators further may include haptic indicators 46. The haptic indicators 46 may be configured as vibration generators that provide vibration indications as alerts pertaining to aspects of device state and operation.

The control system 20 further may be in electronic communication with an input interface 45. The input interface may be configured as an electronic control panel that permits user inputs for control of the exoskeleton device. The input interface may include and one or more control inputs 48 that may provide a varied array of control options for a user, including a power button for turning on and enabling the exoskeleton device.

The described exoskeleton device can be controlled in a manner that performs control methods for automated assessment of user performance and resultant automated adjustment of the device components based on such automated assessment. The control methods may be performed by the control system 20, for example via the processor components control circuit 22 and/or processor 24, executing the program code embodying the exoskeleton control application 26 stored on a non-transitory computer readable medium. In general, therefore, aspects of the invention are directed to enhanced methods of controlling a mobility device having a plurality of mobility device components including at least one actuator component that drives at least one joint component, as well as a plurality of sensors to detect a state of the at least actuator component and joint component. Although the exemplary control methods are described below as a specific order of executing functional logic steps, the order of executing the steps may be changed relative to the order described. Also, two or more steps described in succession may be executed concurrently or with partial concurrence. It is understood that all such variations are within the scope of the present invention.

A generalized control method in a mobility assistance device employing automated assessment and adjustment may employ the following general steps: (1) receiving a command in the control system of the mobility device for initiating an automated assessment and adjustment protocol; (2) controlling one or more mobility device components to perform the automated assessment; (3) electronically gathering user performance data associated with the automated assessment and determining user performance metrics; and (4) electronically controlling one or more of the mobility device components to automatically adjust the one or more mobility device components based on the performance metrics.

In the first step of the general control method, an automated assessment and adjustment protocol may be initiated in a variety of ways utilizing the interface components associated with the control system of the mobility device. For example, a dedicated control button of one of the control inputs 48 on the interface 45 may be employed. Another way to initiate such a protocol may be for the mobility device to receive an initiation command from an external device via the communications interface 32. For example, a device user or clinician may initiate a protocol using a mobile application on a portable communication device, such as a smartphone, tablet computer, or the like.

In the second step of the control method, once an automated assessment and adjustment protocol is initiated, the device control system may control one or more of the mobility device components, and particularly one or more joint components to perform an automated assessment. The automated assessment may be performed by controlling one or more mobility device components to perform a predetermined assessment activity related to performance of the mobility device and/or user. The one or more mobility device components further may be controlled to perform the predetermined assessment activity for a predetermined amount of time. In an exemplary embodiment, the device control system of an exoskeleton device may control one or more of the mobility device components to perform the Manual Muscle Test (MMT) described above.

For example, a single input may be applied to the exoskeleton device (the device user may be both the test administrator and test subject in this case) to start the MMT while standing. The control system of the exoskeleton device may then control the device components to instruct the user to begin moving. Joint components may then be controlled to eliminate and allow for gravity effects as needed as is done in a conventional manual MMT, but instead of body positioning, the force effects associated with the MMT are achieved by controlling the tension or resistance of the device components itself. Accordingly, the control system controls the joint components to provide increasing resistance to motion with each subsequent movement, and the sensors can gather data on affected joint torque and joint motion that the user can apply.

In the third step of the control method, therefore, the control system electronically gathers user performance data associated with the automated assessment and determines user performance metrics. In the example of an automated MMT, the control system may determine muscle grade based on contraction strength, and combine muscle grade results with any other pertinent user information to evaluate user performance and muscle strength as would be typical of a manual MMT. In this manner, the exoskeleton device performs the MMT in a fully automated manner without the use of additional personnel or equipment as used in the conventional manual MMT. The control system can then operate to store the combined results, such as in the memory 30 in the device itself, or transmit results to an external device via the communications interface 32. The information can then be used for future evaluation of the user independently of current device use.

As further described below, the results may then be used to provide automated adjustments to the device components to enhance subsequent user performance (the fourth step in the general control method). In general, example adjustments may include adjusting the assistance level of the mobility device. For example, the assistance level of the joint components may be adjusted to provide more assistance to promote walking, or to provide less assistance to promote strength. If a first level of assistance had been provided previously, and walking frequency has decreased, then the previous setting of the first level of assistance may have been too difficult and assistance could be increased to a second level of assistance to promote walking. Conversely, if a first level of assistance had been provided previously, but muscle strength has decreased, then the previous setting of the first level of assistance may have been too easy and assistance could be decreased to a third level of assistance to promote strength. In this manner, the device may implement targeted strength building exercises based on the assessment results, or notify a healthcare provider if user strength or performance deteriorates over time.

In another exemplary embodiment, the device control system of an exoskeleton device may control one or more of the mobility device components to perform the 10 Meter Walk Test (10MWT) described above. For example, a single input may be applied to the exoskeleton device (the device user again may be both the test administrator and test subject in this case) to start the 10MWT while standing. The control system of the exoskeleton device may then control the device components to instruct the user to begin walking. Based on operation of the device sensors, the control system may then determine when the user has reached a constant speed or cadence and begin an internal counter, comparable to a typical "stopwatch" usage, to track time. The control system may then perform calculations to track the distance covered, and stop the counter when at a ten-meter distance.

Similarly as above, in the third step of the control method the control system electronically gathers user performance data associated with the automated assessment and determines user performance metrics. In the example of an automated 10MWT, the control system may calculate the average speed automatically, and combine walking speed results with any other pertinent user information to evaluate user performance while walking as would be typical of a manual 10MWT. In this manner, the exoskeleton device performs the 10MWT in a fully automated manner without the use of additional personnel or equipment as used in the conventional manual 10MWT. Similarly as above for the MMT, for the 10MWT the control system can then operate to store the combined results, such as in the memory 30 in the device itself, or transmit results to an external device via the communications interface 32. The information can then be used for future evaluation of the user independently of current device use.

As referenced above, the results may then be used to provide automated adjustments to the device components to enhance subsequent user performance (the fourth step in the general control method). In general, example adjustments for the 10MWT may be comparable to those described above for the MMT. In general, example adjustments may include adjusting the assistance level of the mobility device. For example, the assistance level of the joint components may be adjusted to provide more assistance to promote walking, or to provide less assistance to promote strength. If a first level of assistance had been provided previously, and walking frequency has decreased, then the previous setting of the first level of assistance may have been too difficult and assistance could be increased to a second level of assistance to promote walking. Conversely, if a first level of assistance had been provided previously, but muscle strength has decreased, then the previous setting of the first level of assistance may have been too easy and assistance could be decreased to a third level of assistance to promote strength. In this manner, the device may implement targeted strength building exercises based on the assessment results, or notify a healthcare provider if user strength or performance deteriorates over time.

In addition to adjustments similarly performed for the MMT, other example adjustments may be performed that relate more specifically to performance of the 10MWT. Additional example adjustments may include modifications of device settings, such as for example step speed, step height, or step duration, step length, and the like in an attempt to improve 10MWT times. Overall, such adjustments may be employed to improve step symmetry and gait. If a user demonstrates a certain level of proficiency during the assessment, the control system may operate the exoskeleton device to unlock advanced settings for particular modes, or make other modes of operation available, as may be commensurate with increased user physical capabilities. As another manner of operation, control system may operate the exoskeleton device to output alerts, such as via the electronic indicators 40, to "remind" or instruct the user regarding device operation, such as for example to remind the user to walk more frequently, set goals for subsequent assessment tests, transmit test results to a third party for analysis, and the like.

In the above examples, the mobility device is a legged mobility or exoskeleton device. As referenced previously, comparable principles may be applied to suitable mobility assistance devices generally, such as prosthetics, orthotics, and exoskeletons for both the upper and lower extremity.

Similarly, the MMT and 10MWT also are non-limiting examples of assessments, and comparable principles may be applied to other assessments that are currently known or may be developed in the feature. Automated assessments and related automated adjustments may be derived for assessments referenced in the background section of the current specification, and generally may include Rehabilitation Measures, Outcome Measures, Functional Measures, and the like as are known to those of ordinary skill in the art. Choosing which assessments are automated and how that automation is performed will depend highly on the capability of a given device, and the impairment of a given user. Generally, the scope of automated assessment and automated adjustment as described herein encompasses observation or utilization of assistance device interfaces, sensors, actuators, indicators and/or control systems during a specific activity or time period which is intended to indicate the nature, quality, or ability of the device user or of the device itself. In this regard, the present invention enables the gathering of additional information while performing either a known standard assessment (e.g., MMT or 10MWT) or emergent assessments that may be developed as mentioned above. For example, one could gather information on step symmetry while the 10MWT is explored, and such an Investigation of step symmetry could lead to the emergence of a new standard assessment—e.g., a "Step Symmetry" assessment, enabled by the present invention. Traditionally, such assessments would require dedicated hardware or methods, but in the context of the present invention, the mobility device is instead utilized in a fully automated manner to accommodate any future emergent assessments.

Additional details will now be described as to the fourth step in the general automated assessment and adjustment method, which again is controlling one or more of the mobility device components to automatically adjust the one or more mobility device components. In exemplary embodiments, adjustments that may be implemented by the control system may be characterized as either "low-level adjustments" or "high-level adjustments". Low-level adjustments may relate to affecting operation of individual or groups of mobility device components including the sensors, actuators, interfaces, and electronic controllers of the mobility device to control specific performance of such components. High-level adjustments may include the controlled combination of a plurality of low-level adjustments for performance of a broader healthcare function. High-level adjustments, for example, may be implemented to perform diagnosis operations to assess user impairment, treatment operations to improve of user performance and physical capabilities, and capability assessments of the user and/or of the mobility device itself.

In accordance with the above, a first category of low-level adjustments may include sensor adjustments. Examples of sensor adjustments include (without limitation): selecting which or when sensors are on or off; selecting which or when sensors are active or passive from an electronic control standpoint; increasing or decreasing sensor amplification or attenuation; combining or recombining sensor outputs; and selecting and setting sensor associations with particular actuator and/or interface components. A second category of low-level adjustments may include actuator adjustments. Examples of actuator adjustments include (without limitation): selecting which or when actuators are on or off; selecting which or when actuators are active or passive from an energetic standpoint; increasing or decreasing actuator assistance or resistance levels; combining or recombining actuator outputs; and selecting and setting actuator associations with particular sensor and interface components. A third category of low-level adjustments may include interface adjustments. Examples of interface adjustments include (without limitation): selecting which or when interface components are on or off; selecting which or when information or feedback is provided; recruiting other interfaces to present similar or other feedback or information; and providing or denying feedback or information through a given interface component.

These low-level adjustments, affecting mobility device sensors, actuators, and interfaces, are orchestrated by the device control system. The control system may implement the low-level adjustments independently, interdependently with other low-level adjustments, or time dependently. Such low-level adjustments are made in response to an automated assessment (control method steps (1)-(3)), and a plurality of low-level adjustments may be selectively grouped and implemented to perform a high-level adjustment, which promotes user and device capability and thereby can alter and improve subsequent assessment outcomes.

Accordingly, similarly as the low-level adjustments, different categories of high-level adjustments may be performed. In exemplary embodiments, a first category of high-level adjustments may include balance, stability, and spasticity adjustments. Examples of balance, stability, and spasticity adjustments include (without limitation): isolating movement of certain device components, or providing feedback, to enable balance or stability or control spasticity; perturbing movement of particular device components, or providing feedback, to develop balance or stability or reduce spasticity; prompting user physical activity or a specific exercise to maintain or further develop balance, stability, or spasticity; and prompting repeated assessment to track balance, stability, or spasticity changes. A second category of high-level adjustments may include coordination and dexterity adjustments. Examples of coordination and dexterity adjustments include (without limitation): organizing motion through operation of multiple device components, or providing feedback, to enable coordination or dexterity; disorganizing motion through operation of multiple device components, or providing feedback, to develop coordination or dexterity; promoting user physical activity or a specific exercise to maintain, or further develop, coordination or dexterity; and prompting repeated assessment to track coordination or dexterity changes. A third category of high-level adjustments may include strength and mobility adjustments. Examples of strength and mobility adjustments include (without limitation): controlling device components to assist motion at a determined level to enable strength or mobility improvement; controlling device components to resist motion to develop strength or mobility; prompting user physical activity or a specific exercise to maintain, or further develop, strength or mobility; and prompting repeated assessment to track strength or mobility changes. A fourth category of high-level adjustments may include capability and independence adjustments. Examples of capability and independence adjustments include (without limitation): enabling device function and controlling device components to promote enhanced user capability or independence; disabling device function to develop capability or independence; prompting user physical activity or exercise to maintain or further develop capability or independence; and tracking activities or location to assess capability and independence changes.

These high-level adjustments also are orchestrated by the device control system. Choosing which high-level adjustments are automated and how that automation is performed generally will depend on the capability of a given device, and the indications of a given assessment. The automated high-level adjustments referred to herein typically involve modulation or modification of multiple mobility device components combining low-level adjustments to specific interface components, sensors, actuators, and/or control devices in response to an assessment which is intended to alter the nature, quality, or ability of the device user and/or the device itself. The device adjustments further may be combined with additional therapeutic operations. One such additional operation may be application or adjustment to application of functional electrical stimulation (FES).

While the above description largely has focused on automated assessment and adjustment pertinent to user impairment, automated assessment and adjustment may also be applied to device composition, state, performance, or utilization of the mobility device itself. Such assessments may pertain to device specific indications, such as for example:

hardware versions, software/firmware versions, sensor output (e.g. range checking), actuator output (e.g. motor current), power level (e.g. battery percentage), wireless connectivity (e.g. Bluetooth strength), device location, device use (e.g. session count), or device service life (e.g. joint cycles). These assessments may be associated with the low-level and high-level adjustments, or pertain to device specific alterations, such as for example: enabling or disabling device function(s), increasing or decreasing actuator output, providing warnings or alerts, creating diagnostic or performance reports, and transmitting information about user and device performance to external electronic devices.

With the control system and methods of the present invention, the control system of a mobility device operates to leverage device sensors, actuators, and interfaces to perform automated assessment of user impairment and device status, and to make automated adjustments to the state and/or operation of the mobility device components to improve assessment outcomes and overall device and user performance. Rather than simply compensating for impairment as is done conventionally, mobility assistance devices in accordance with the present invention perform automated assessment of the individual user, and perform automated adjustment of device component state and/or operation to enhance the user's recovery or physical capability. By providing for automated assessment and adjustment of the mobility assistance device, there is reduced need for specialized equipment, expert personnel, and additional external equipment for assessment and adjustment, while allowing the mobility assistance device to play a broader role in the management of impairments for which the device traditionally has only compensated. In other words, in addition to the traditional role of compensating for impairment, the mobility assistance device of the present invention can improve and optimize user performance through automated assessment and adjustment of the mobility assistance device.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A control method of controlling a mobility device having a plurality of mobility device components including at least one actuator component that drives at least one joint component, the control method comprising the steps of:
    providing said mobility device, said mobility device further including a control system for controlling operation of the plurality of mobility device components to selectively configure and modulate the at least one joint component;
    providing within said mobility device a control application to be executed by the control system;
    providing within said mobility device a plurality of sensors to detect a state of the at least one actuator component and/or the at least one joint component; and
    executing the control application with the control system to perform the steps of:
    receiving a command in the control system of the mobility device for initiating an automated assessment and adjustment protocol;
    controlling one or more of the plurality of mobility device components to perform the automated assessment by controlling one or more of the plurality of mobility device components to perform a plurality of predetermined assessment operations;
    electronically gathering user performance data comprising operation of the mobility device in connection with performance of the predetermined assessment operations, and determining user performance metrics corresponding to user capabilities in using the mobility device in connection with performance of the predetermined assessment operations; and
    electronically adjusting the control of one or more of the plurality of mobility device components in accordance with the performance metrics to enhance user performance with the mobility device;
    wherein the automated assessment comprises an automated manual muscle test (MMT), and controlling one or more of the plurality of mobility device components to perform the automated assessment comprises:
    controlling the plurality of mobility device components for the user to begin moving; and
    controlling the at least one joint component to eliminate and allow for gravity effects in accordance with the MMT by controlling the tension or resistance of the at least one joint component.

2. The control method of claim 1, wherein electronically gathering user performance data comprises:
    determining muscle grade results based on contraction strength; and
    combining the muscle grade results with user information to evaluate user muscle strength in accordance with the MMT.

3. A control method of controlling a mobility device having a plurality of mobility device components including at least one actuator component that drives at least one joint component, the control method comprising the steps of:
    providing said mobility device, said mobility device further including a control system for controlling operation of the plurality of mobility device components to selectively configure and modulate the at least one joint component;
    providing within said mobility device a control application to be executed by the control system;
    providing within said mobility device a plurality of sensors to detect a state of the at least one actuator component and/or the at least one joint component; and
    executing the control application with the control system to perform the steps of:
    receiving a command in the control system of the mobility device for initiating an automated assessment and adjustment protocol;
    controlling one or more of the plurality of mobility device components to perform the automated assessment by controlling one or more of the plurality of mobility device components to perform a plurality of predetermined assessment operations;

electronically gathering user performance data comprising operation of the mobility device in connection with performance of the predetermined assessment operations, and determining user performance metrics corresponding to user capabilities in using the mobility device in connection with performance of the predetermined assessment operations; and electronically adjusting the control of one or more of the plurality of mobility device components in accordance with the performance metrics to enhance user performance with the mobility device;

wherein the automated assessment comprises an automated 10 Meter Walk Test (10MWT), and controlling one or more of the plurality of mobility device components to perform the automated assessment comprises:

controlling the plurality of mobility device components for the user to begin walking;

determining when the user has reached a constant speed and begin an internal counter; and tracking a distance covered by the user and stopping the internal counter when at a fixed distance.

4. The control method of claim 3, wherein electronically gathering user performance data comprises:

calculating a gait parameter related to walking automatically, and combining gait parameter results with user information to evaluate user performance while walking in accordance with the 10MWT.

5. The control method of claim 1, wherein electronically controlling one or more of the plurality of mobility device components comprises adjusting an assistance level the at least one joint component to provide more assistance to promote walking, or to provide less assistance to promote strength.

6. The control method of claim 5, further comprising:

when a first level of assistance has been provided previously and walking frequency has decreased, increasing the assistance level to a second assistance level to promote walking; and when the first level of assistance has been provided previously and muscle strength has decreased, decreasing the assistance level to a third assistance level to promote muscle strength.

7. The control method of claim 3, wherein electronically controlling one or more of the plurality of mobility device components comprises modifying the plurality of mobility device components to adjust at least one of step speed, step height, step duration, or step length.

8. A non-transitory computer readable medium storing program code for a control application for use in controlling a mobility device including a plurality of mobility device components comprising at least one drive component that drives at least one joint component, wherein the control application includes program code for an automated assessment and adjustment protocol comprising a plurality of predetermined assessment operations to control one or more of the plurality of mobility device components;

wherein the mobility device comprises: an electronic control system for controlling operation of the at least one drive component to selectively configure and modulate the at least one joint component, and a plurality of sensors to detect a state of the at least one drive component and/or the at least one joint component; and the program code when executed by the electronic controller performs the steps of:

receiving a command in the control system of the mobility device for executing the control application to initiate the automated assessment and adjustment protocol comprising the plurality of predetermined assessment operations;

in response to receiving the command, controlling one or more of the plurality of mobility device components to perform the automated assessment and adjustment protocol by controlling one or more of the plurality of mobility device components to perform the plurality of predetermined assessment operations;

electronically gathering user performance data comprising operation of the mobility device in connection with performance of the predetermined assessment operations;

determining user performance metrics corresponding to user capabilities in using the mobility device when performing the predetermined assessment operations; and electronically adjusting the control of one or more of the plurality of mobility device components in accordance with the performance metrics to enhance user performance with the mobility device;

wherein the automated assessment comprises an automated manual muscle test (MMT), and controlling one or more of the plurality of mobility device components to perform the automated assessment comprises: controlling the plurality of mobility device components for the user to begin moving, and controlling the at least one joint component to eliminate and allow for gravity effects in accordance with the MMT by controlling the tension or resistance of the at least one joint component.

9. The non-transitory computer readable medium of claim 8, wherein electronically gathering user performance data comprises:

determining muscle grade results based on contraction strength; and combining the muscle grade results with user information to evaluate user muscle strength in accordance with the MMT.

10. The non-transitory computer readable medium of claim 8, wherein electronically controlling one or more of the mobility device components comprises adjusting an assistance level of the at least one joint component to provide more assistance to promote walking, or to provide less assistance to promote strength.

11. The non-transitory computer readable medium of claim 10, further comprising:

when a first level of assistance has been provided previously and walking frequency has decreased, increasing the assistance level to a second assistance level to promote walking; and when the first level of assistance has been provided previously and muscle strength has decreased, decreasing the assistance level to a third assistance level to promote muscle strength.

12. A mobility device comprising:

at least one drive component that drives at least one joint component;

an electronic control system for controlling operation of the at least one drive component to selectively configure and modulate the at least one joint component;

a plurality of sensors to detect a state of the at least one drive component and/or the at least one joint component; and the non-transitory computer readable medium according to claim 8, wherein the electronic control system executes the program code stored on the non-transitory computer readable medium.

13. A non-transitory computer readable medium storing program code for a control application for use in controlling a mobility device including a plurality of mobility device components comprising at least one drive component that drives at least one joint component, wherein the control application includes program code for an automated assessment and adjustment protocol comprising a plurality of predetermined assessment operations to control one or more of the plurality of mobility device components;

wherein the mobility device comprises: an electronic control system for controlling operation of the at least one drive component to selectively configure and modulate the at least one joint component, and a plurality of sensors to detect a state of the at least one drive component and/or the at least one joint component; and the program code when executed by the electronic controller performs the steps of:

receiving a command in the control system of the mobility device for executing the control application to initiate the automated assessment and adjustment protocol comprising the plurality of predetermined assessment operations;

in response to receiving the command, controlling one or more of the plurality of mobility device components to perform the automated assessment and adjustment protocol by controlling one or more of the plurality of mobility device components to perform the plurality of predetermined assessment operations;

electronically gathering user performance data comprising operation of the mobility device in connection with performance of the predetermined assessment operations;

determining user performance metrics corresponding to user capabilities in using the mobility device when performing the predetermined assessment operations; and electronically adjusting the control of one or more of the plurality of mobility device components in accordance with the performance metrics to enhance user performance with the mobility device;

wherein the automated assessment comprises an automated 10 Meter Walk Test (10MWT), and controlling one or more of the plurality of mobility device components to perform the automated assessment comprises: controlling the plurality of mobility device components for the user to begin walking, determining when the user has reached a constant speed and begin an internal counter, and tracking a distance covered by the user and stopping the internal counter when at a fixed distance.

14. The non-transitory computer readable medium of claim 13, wherein electronically gathering user performance data comprises:

calculating a gait parameter related to walking automatically, and combining gait parameter results with user information to evaluate user performance while walking in accordance with the 10MWT.

15. The non-transitory computer readable medium of claim 13, wherein controlling one or more of the mobility device components comprises modifying the mobility device components to adjust at least one of step speed, step height, step duration, or step length.

16. A mobility device comprising:

at least one drive component that drives at least one joint component;

an electronic control system for controlling operation of the at least one drive component to selectively configure and modulate the at least one joint component;

a plurality of sensors to detect a state of the at least one drive component and/or the at least one joint component; and the non-transitory computer readable medium according to claim 13, wherein the electronic control system executes the program code stored on the non-transitory computer readable medium.

* * * * *